United States Patent [19]

Bay

[11] Patent Number: 4,760,191
[45] Date of Patent: Jul. 26, 1988

[54] PREPARATION OF BIS(4-HALOPHENYL)PHENYLPHOSPHINE OXIDE

[75] Inventor: Elliott Bay, Ridgefield, Conn.

[73] Assignee: Akzo America Inc., New York, N.Y.

[21] Appl. No.: 914,911

[22] Filed: Oct. 3, 1986

[51] Int. Cl.$^4$ ............................................. C07F 9/02
[52] U.S. Cl. ............................................. 568/14
[58] Field of Search ............................................. 568/14

[56] References Cited

U.S. PATENT DOCUMENTS

| | | | |
|---|---|---|---|
| 3,532,774 | 10/1970 | Maier | 568/14 X |
| 3,624,159 | 11/1971 | Dagani | 568/14 |
| 3,763,241 | 10/1973 | Dagani | 568/14 |
| 3,927,113 | 12/1975 | Reuter et al. | 568/14 X |
| 4,032,603 | 6/1977 | Kaschuba et al. | 568/14 X |
| 4,642,366 | 2/1987 | Honig et al. | 558/138 |

OTHER PUBLICATIONS

"Organic Synthesis", 54, pp. 63–67 (1984).
"Canadian J. of Chem.", 46, pp., 86–87 (1968).

*Primary Examiner*—Paul F. Shaver
*Attorney, Agent, or Firm*—Richard P. Fennelly; Louis A. Morris; Frank W. Young

[57] ABSTRACT

The invention is the preparation of bis(4-halophenyl)-phenylphosphine oxide from phenylphosphorus dihalide by a method wherein the dihalide is reacted with 4-halophenyl magnesium to produce the phosphine which is oxidized using alcohol in the presence of a halocarbon solvent to produce the phosphine oxide product of this invention.

11 Claims, No Drawings

PREPARATION OF BIS(4-HALOPHENYL)PHENYLPHOSPHINE OXIDE

BACKGROUND OF THE INVENTION

The present invention relates to the process of preparing bis(4-halophenyl)phenylphosphine oxide.

RELATED ART

Phosphine oxides represent a class of compounds of commercial importance in the detergent and cosmetics fields as additives to oils, lubricants, detergents, and as surface active agents. They also possess biocidal properties and may be utilized, for example, as herbicides, insecticides, fungicides, and bactericides. In addition, they form with metals and metal salts, especially with transition metal salts, soluble complex compounds and may be utilized, for example, for the extraction of uranium salts and as monomer in various engineering plastics.

Phosphine oxides can be prepared by the oxidation of phosphines which, in turn, can be prepared by the reaction of various phosphorus mono-halides with Grignard reagents. The direct oxidation of phosphines, especially tertiary phosphines and particularly the alkyl phosphines, with oxygen, yield complex mixtures of the desirous phosphine oxide, phosphonites, phosphonates and phosphates. Such reactions are therefore not generally suited for the preparation of the desirable phosphine oxide product in high yields.

Various other means for oxidizing phosphines, particularly tertiary phosphines, to the corresponding phosphine oxide without the formation of these undesirable products, have been proposed. For example, U.S. Pat. No. 3,532,774 to Maier discloses a method of preparing phosphonites and phosphine oxides. The phosphine oxides in the process of the invention are prepared by heating an aminophosphine with an equal amount of an alcohol in the presence of an isomerization catalyst. It is indicated that in the absence of the catalyst, the phosphonite is formed.

U.S. Pat. No. 3,760,000 discloses the preparation of phosphine oxides by the catalytic oxidation of tertiary phosphines. The process disclosed comprises the reaction of a tertiary phosphine with a zero valent palladium compound and oxygen at a temperature from 0° C. to 60° C. U.S. Pat. No. 3,852,362 discloses the preparation of tertiary organo phosphine oxides. The process disclosed is the reaction of a primary, secondary, or tertiary organophosphine with an aqueous alkali.

A commercial process for preparing tertiary phosphine oxides in general, and bis(4-chlorophenyl)phenylphosphine oxide) in particular, comprise oxidation of the tertiary phosphine by aqueous hydrogen peroxide. Such a process is described in an article entitled, "Synthesis of Some Tertiary Substituted Arylphosphines" appearing in *Phosphorus*, Vol. 5, pp. 43–45, 1974 (Gordon & Bush Science Pub.). Yields using the $H_2O_2$ process are in the 60% range. This process, however, has several disadvantages such as the difficulties and hazards of handling $H_2O_2$ and the need for extraction of the product phosphine oxide from aqueous media.

SUMMARY OF THE INVENTION

The invention comprises the preparation of bis(4-halophenyl)phenylphosphine oxide by reacting 4-halophenyl magnesium halide with phenylphosphorus dihalide, and the oxidation of the phosphine formed thereby in the presence of at least one alcohol and a halocarbon solvent.

DETAILED DESCRIPTION OF THE INVENTION

Bis(4-halophenyl)phenylphosphine oxide is prepared by reacting at reflux in a solvent bis(4-halophenyl)phenylphosphine with an alcohol wherein the alcohol and the solvent are present in amounts sufficient to produce the desired product. The phosphine compound which, in the instant invention, is oxidized to the phosphine oxide can be prepared by a variety of methods as are disclosed in *Organophosphorus Compounds* by Koslopoff, Chapter 2, pages 10–41 (1950), J. Wiley & Sons Inc. Pub.

In the preferred method of preparing the phosphine of this invention, a 4-halophenyl magnesium halide (a Grignard reagent) is reacted with phenylphosphorus dihalide to give bis(4-halophenyl)phenylphosphine.

In the practice of the invention, the phosphine compound is reacted with at least one alcohol and a solvent wherein both the alcohol and solvent are preferably utilized in amounts in excess of stoichiometric quantities. Amounts of alcohol which can be used in practicing the invention can range from about 100% to about 2000% and preferably from about 50% to about 100% in excess of stoichiometric quantities. Amounts of the halocarbon solvent can range from about 100% to about 2000% and preferably from about 200% to about 500% in excess of stoichiometric quantities.

Alcohols suitable for use in practicing the invention have the formula $R'(OH)_n$, wherein $R'$ can be aliphatic radical of from about $C_1$ to about $C_8$ and where n is 1 or 2. The oxidation of the phosphine is carried out at reflux temperatures. Examples of such alcohols are methanol, ethanol, propanol, and ethylene glycol.

Suitable halocarbon solvents for practicing the invention are perhalocarbons. Examples of such solvents are carbon tetrachloride and hexachloroethane.

The following example is descriptive of an embodiment of the present invention.

EXAMPLE 1

Preparation of 4,4'-Bis(Chlorophenyl)Phenylphosphine Oxide

Magnesium turnings (24.3 g, 1.0 mole) were placed in a dry 2-liter, 4-neck flask fitted with an overhead stirrer, thermometer, reflux condenser, and 500 ml addition funnel, under a nitrogen atmosphere. The addition funnel was charged with 1,4-dichlorobenzene (150 g, 1.02 moles) dissolved in dry tetrahydrofuran (220 ml). Approximately 20 ml of this solution was added to the magnesium turnings.

The reaction was initiated with a small crystal of iodine. The remainder of the solution in the addition funnel was added dropwise with stirring so that the reaction temperature did not exceed 95° C. (1.5 hours). The reaction mixture was heated to reflux for 2 hours after addition was complete. The reaction was cooled to room temperature and dry tetrahydrofuran (150 ml) added. The solution was allowed to settle and the liquid was siphoned away from the solids into a dry 2-L reaction assembly identical to the previous one. The addition funnel on the second reaction assembly was charged with a solution of phenylphosphonous dichloride (80.6 g, 0.45 mole) and tetrahydrofuran (370 ml).

This solution was added slowly with stirring so that the reaction temperature stayed below 30° C. The reaction was stirred at room temperature for 1 hour after addition was complete. Water (108 g, 6 mole) was placed in the addition funnel and added dropwise. The hydrated magnesium salts precipitated and the solution filtered through a sinter glass funnel. The tetrahydrofuran solvent was stripped off and thick yellow oil which remained was placed in a 2-liter flask and dissolved in a mixture of carbon tetrachloride (225 ml) and methanol (225 ml). The flask was fitted with a reflux condenser and the solution refluxed with magnetic stirring for 18 hours. The volatiles were removed by rotary evaporation giving a product yield of 158.9 g or 79% yield.

I claim:

1. A process for preparing bis(4-halophenyl)phenylphosphine oxide comprising reacting at reflux temperatures at least one alcohol with bis(4-halophenyl)phenylphosphine in the presence of a halocarbon solvent.

2. The process of claim 1 wherein the reaction is accomplished in the presence of an excess of alcohol.

3. The process of claim 2 wherein the alcohol is methanol.

4. The process of claim 2 wherrein the excess ranges from about 100% to 2000% in excess of stiochiometric quantities.

5. The process of claim 1 wherein the reaction is accomplished in the presence of an excess of a halocarbon solvent.

6. The process of claim 5 wherein the solvent is carbon tetrachloride.

7. The process of claim 4 wherein the excess ranges from about 100% to about 2000% in excess of stoichiometric quantities.

8. The process of claim 1 wherein the bis(4-halophenyl)phenylphosphine is prepared by the reaction of phenylphosphorus dihalide with 4-halophenyl magnesium halide.

9. A process for preparing bis(4-halophenyl)phenylphosphine oxide from phenylphosphorus dihalide comprising reacting phenylphosphoru dihalide with 4-halophenyl magnesium halide to produce bis(4-halophenyl) phenylphosphine which is oxidized to the oxide by reflux with at least one alcohol in the presence of a halocarbon solvent.

10. The process of claim 9 wherein the solvent is carbon tetrachloride.

11. The process of claim 9 wherein the alcohol is methanol.

* * * * *